United States Patent [19]

Fahmy

[11] 4,428,945
[45] * Jan. 31, 1984

[54] O-ALKYL S-(TERTIARY ALKYL) ALKYLPHOSPHONOTHIOATE INSECTICIDES AND NEMATOCIDES

[75] Inventor: Mohamed A. Fahmy, Princeton, N.J.

[73] Assignee: Rhone-Poulenc Agrochimie, Lyons, France

[*] Notice: The portion of the term of this patent subsequent to May 19, 1998 has been disclaimed.

[21] Appl. No.: 359,356

[22] Filed: Mar. 18, 1982

Related U.S. Application Data

[63] Continuation of Ser. No. 209,093, Nov. 21, 1980, abandoned.

[51] Int. Cl.³ .......................... A01N 57/20; C07F 9/40
[52] U.S. Cl. ....................................... 424/222; 260/961
[58] Field of Search .......................... 260/961; 424/222

[56] References Cited

U.S. PATENT DOCUMENTS

| | | | |
|---|---|---|---|
| 2,934,507 | 4/1960 | Chadwick | 260/23 |
| 3,139,449 | 6/1964 | Ahramjian | 260/454 |
| 3,166,505 | 1/1965 | Kirby | 252/49.8 |
| 3,208,943 | 9/1965 | Kirby | 252/49.8 |
| 3,209,020 | 9/1965 | Schrader | 260/941 |
| 3,856,896 | 12/1974 | Hagarty | 424/219 |
| 4,257,987 | 3/1981 | Arend et al. | 424/219 |
| 4,268,508 | 3/1981 | Fahmy | 260/961 |
| 4,327,040 | 4/1982 | Arend et al. | 260/973 |

*Primary Examiner*—Anton H. Sutto
*Attorney, Agent, or Firm*—Burns, Doane, Swecker & Mathis

[57] ABSTRACT

Compounds having the formula

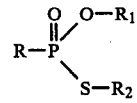

in which
R is an alkyl of 1 to 8 carbon atoms, haloalkyl of 1 to carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is tertiary alkyl of 4 to 8 carbon atoms are disclosed as well as their use as insecticides and nematocides, e.g. in controlling corn rootworm and Southern Armyworm.

40 Claims, No Drawings

O-ALKYL S-(TERTIARY ALKYL) ALKYLPHOSPHONOTHIOATE INSECTICIDES AND NEMATOCIDES

This application is a continuation, of application Ser. No. 209,093, filed Nov. 21, 1980, now abandoned.

CROSS-REFERENCE TO RELATED APPLICATIONS

An application entitled "O-ALKYL S-BRANCHED ALKYL ALKYLPHOSPHONODITHIOATE INSECTICIDES AND NEMATOCIDES" Ser. No. 107,819, filed Dec. 28, 1979, in the name of Mohamed A. Fahmy, discloses certain O-alkyl S-(branched alkyl) alkylphosphonodithioates.

SUMMARY OF THE INVENTION

This invention relates to O-alkyl S-(tertiary alkyl) alkylphosphonothioate compounds and their use as insecticides and nematocides.

More particularly, the compounds of the invention have the formula

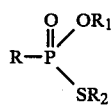

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is alkyl of 1 to 8 carbon atoms; and
$R_2$ is tertiary alkyl of 4 to 8 carbon atoms.

These compounds exhibit a wide range of insecticidal and nematocidal activity and are of particular interest in controlling corn rootworm because of their excellent activity against this pest and their long residual soil activity.

DETAILED DESCRIPTION OF THE INVENTION

An important structural feature of the compounds of this invention is that $R_2$ in the above formula is tertiary alkyl. Certain alkylphosphonothioate insecticides are described in the prior art, such as in U.S. Pat. No. 3,209,020. However, none of the species described in the patent or the other known prior art correspond to the above formula where $R_2$ is tertiary alkyl.

It has been found that the S-tertiary alkyl compounds of this invention possess unexpected advantageous properties. For example, they exhibit excellent stability and long residual activity particularly in soil. Since the activity of the S-tertiary alkyl compounds against corn rootworm is good and residual activity in soil is long the compounds of this invention are of special interest for controlling corn rootworm.

The compounds disclosed herein can be prepared by the methods known to those in the art. Preferably, the compounds of this invention are prepared from a starting material which is S-alkyl alkylphosphonothioic halide, the preparation of which is illustrated in Example 1. The S-(tertiary alkyl) alkylphosphonothioic halide is reacted with an alcohol in the presence of a base to arrive at the compounds of this invention.

The preferred reaction scheme is as follows:

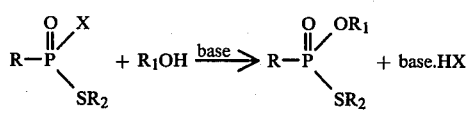

in which
R is alkyl of 1 to 8 carbon atoms haloalykl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is alkyl of 1 to 8 carbon atoms;
$R_2$ is tertiary alkyl of 4 to 8 carbon atoms; and
X is halogen, preferably Cl.

The reaction is advantageously carried out at a temperature of about 0° C. to 100° C. in an organic solvent in the presence of a tertiary amine, aqueous base, such as aqueous NaOH, or by producing the alkali salt of the alcohol using alkali metals such as sodium.

Suitable organic solvents are, for example, benzene, toluene, cyclohexane and 2-butanone, or the alcohol itself.

Suitable tertiary amines include trimethylamine, triethylamine, dimethylaniline, diethylaniline and pyridine.

The alkylphosphonothioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 kg/hectare. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting or after planting but before sprouting has taken place or after sprouting.

The following examples illustrate the preparation of the compounds of this invention and their pesticidal preparations. It will be understood that all of the compounds disclosed herein can be prepared by methods analogous to those described below.

EXAMPLE 1

S-tert-butyl ethylphosphonothioic chloride $$\underset{CH_3CH_2-P}{\overset{O}{\underset{\|}{}}}\overset{Cl}{\underset{S-C(CH_3)_3}{}}$$

To a solution of ethylphosphonic dichloride (32.0 g, 0.22 mol) in 300 ml toluene, was added 2-methyl-2-propanethiol (18 g, 0.2 mol). While stirring triethylamine (22 g, 0.22 mol) was added dropwise and the temperature of the reaction was maintained at 30°–35° C. during the addition of the amine. After the complete addition of the amine, the mixture was stirred overnight at room temperature. The amine hydrochloride was filtered and the toluene solution was concentrated under vacuum. Hexane (200 ml) was added and the solution was filtered again.

The solvents were stripped off under vacuum and the residual liquid was distilled. The product (25 g, 72.5% yield) distilled at 72°–73° C./0.7 mm. $^1$H-NMR in chloroform-d-Si (Me)$_4$ confirmed the structure of the title compound.

EXAMPLE 2

Preparation of O-ethyl S-tert.-butyl ethylphosphonothioate

In a solution of S-tert-butyl ethylphosphonothioic chloride (Example 1) (8.0 g, 0.048 mol) in toluene (50 ml) was added a solution of sodium ethoxide (0.04 mol) in ethanol (40 ml). The addition was dropwise, while stirring and the reaction was carried out under nitrogen. Stirring was continued overnight at room temperature, and then approximately 80% of the solvents were removed under vacuum. Toluene (100 ml) was added and the sodium chloride formed from the reaction was filtered. Toluene was stripped off under vacuum and the residual liquid was distilled. The product (5.8 g, 69.6% yield) distilled at 69°–72° C./0.2 mm.

Analysis of $^1$H-NMR spectrum of this product confirmed the structure of the title compound.

EXAMPLES 3–6

In a manner analogous to that of Example 2, the following compounds were prepared.

$$\underset{R-P}{\overset{O}{\underset{\|}{}}}\overset{OR_1}{\underset{SR_2}{}}$$

| Example | R | R$_1$ | R$_2$ | B.p. C./mm |
|---|---|---|---|---|
| 3 | C$_2$H$_5$ | CH$_3$ | t-butyl | 64–67/0.7 |
| 4 | C$_2$H$_5$ | C$_3$H$_7$ | t-butyl | 61–63/0.05 |
| 5 | C$_2$H$_5$ | (CH$_3$)$_2$CH | t-butyl | 42–43/0.05 |
| 6 | C$_2$H$_5$ | C$_2$H$_5$ | t-amyl | 56–58/0.07 |

EXAMPLE 7

Testing for Corn rootworm intrinsic activity, and activity against Southern Armyworm.

A. Corn Rootworm Intrinsic Activity (CRW)

The test compound is prepared in a one percent solution with acetone or ethanol. The stock solution is then diluted with an aqueous solution of Tween-20 and water to the appropriate concentration (i.e., 100, 10, 1, 0.1, 0.005 ppm). Two ml of this solution is pipetted into a 9 cm petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in Table 1.

B. Southern Armyworm Intrinsic Activity (SAW)

Stock solution (1%) of test material was made in acetone and diluted to the desired concentration by a 500 ppm Tween-20 aqueous solution. Lima bean leaves are dipped into the solution and transferred to petri dishes (100×15 mm) containing two filter papers moistened with 2 ml water. Each petri dish contained one leaf and was kept open to dry out the solution on the leaf. Five third instar larvae of Southern Armyworm (*Spodoptera eridania*) were added to the leaf and the dish was finally covered.

The insects were held at 78° F. for 72 hours and percent kill was recorded. The results are tabulated in Table 1.

TABLE 1

| | % Kill | | | | |
|---|---|---|---|---|---|
| | SAw | | CRw Rate (ppm) | | |
| Example | 500 | 100 | 1 | 0.1 | 0.05 |
| 2 | 100 | 100 | 100 | 95 | 75 |
| 3 | 100 | 90 | 100 | 100 | 100 |
| 4 | 100 | 15 | 100 | 70 | — |
| 5 | 80 | 15 | 80 | 45 | — |
| 6 | 100 | 50 | 100 | 95 | 100 |

I claim:

1. A method for controlling insects and nematodes which comprises applying thereto or to their habitat a pesticidal amount of a compound of the formula $$\underset{R-P}{\overset{O}{\underset{\|}{}}}\overset{O-R_1}{\underset{S-R_2}{}}$$

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is a tertiary alkyl of 4 to 8 carbon atoms.

2. The method of claim 1 in which $R_1$ is unbranched alkyl of 1 to 6 carbon atoms.

3. The method of claim 1 in which $R_2$ is t-butyl.

4. The method of claim 1 in which $R_2$ is t-amyl.

5. The method of claim 1 in which R is alkyl of 1 to 8 carbon atoms.

6. The method of claim 1 in which R is methyl or ethyl;
$R_1$ is unbranched; and
$R_2$ is t-butyl or t-amyl.

7. The method of claim 1 in which R is ethyl;
$R_1$ is ethyl; and
$R_2$ is t-butyl.

8. The method of claim 1 in which R is ethyl;
$R_1$ is ethyl; and
$R_2$ is t-amyl.

9. The method of claim 1 in which R is ethyl;
$R_1$ is methyl; and
$R_2$ is t-butyl.

10. The method of claim 1 in which R is methyl;
$R_1$ is methyl; and
$R_2$ is t-butyl.

11. The method of claim 1 in which R is methyl;
$R_1$ is ethyl; and
$R_2$ is t-butyl.

12. The method of claim 1 in which R is methyl;
$R_1$ is n-propyl; and
$R_2$ is t-butyl.

13. The method of claim 1 in which R is ethyl;
$R_1$ is n-propyl; and
$R_2$ is t-butyl.

14. A method for controlling corn rootworm which comprises providing a pesticidal amount in the soil of a compound of the formula

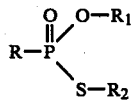

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is a tertiary alkyl of 4 to 8 carbon atoms.

15. A compound of the formula

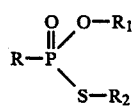

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is tertiary alkyl of 4 to 8 carbon atoms.

16. A compound of claim 15 in which $R_1$ is unbranched alkyl of 1 to 6 carbon atoms.

17. A compound of claim 15 in which $R_2$ is t-butyl.

18. A compound of claim 15 in which $R_2$ is t-amyl.

19. A compound of claim 15 in which R is alkyl of 1 to 8 carbon atoms.

20. A compound of claim 15 in which R is methyl or ethyl;
$R_1$ is unbranched; and
$R_2$ is t-butyl or t-amyl.

21. A compound of claim 15 in which R is ethyl;
$R_1$ is ethyl; and
$R_2$ is t-butyl.

22. A compound of claim 15 in which R is ethyl;
$R_1$ is ethyl; and
$R_2$ is t-amyl.

23. A compound of claim 15 in which R is ethyl;
$R_1$ is methyl; and
$R_2$ is t-butyl.

24. A compound of claim 15 in which R is methyl;
$R_1$ is methyl; and
$R_2$ is t-butyl.

25. A compound of claim 15 in which R is methyl;
$R_1$ is ethyl; and
$R_2$ is t-butyl.

26. A compound of claim 15 in which R is methyl;
$R_1$ is n-propyl; and
$R_2$ is t-butyl.

27. A compound of claim 15 in which R is ethyl;
$R_1$ is n-propyl; and
$R_2$ is t-butyl.

28. A composition comprising as the active ingredient a compound of the formula

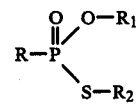

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is tertiary alkyl of 4 to 8 carbon atoms in an amount effective as an insecticide or a nematocide; and
an inert, non-phytotoxic organic solvent or a solid carrier.

29. The composition of claim 28 in which $R_1$ is unbranched alkyl of 1 to 6 carbon atoms.

30. The composition of claim 28 in which $R_2$ is t-butyl.

31. The composition of claim 28 in which $R_2$ is t-amyl.

32. The composition of claim 28 in which R is alkyl of 1 to 8 carbon atoms.

33. The composition of claim 28 in which R is methyl or ethyl;
$R_1$ is unbranched; and
$R_2$ is t-butyl or t-amyl.

34. The composition of claim 28 in which R is ethyl;
$R_1$ is ethyl; and
$R_2$ is t-butyl.

35. The composition of claim 28 in which R is ethyl;

$R_1$ is ethyl; and
$R_2$ is t-amyl.

36. The composition of claim 28 in which R is ethyl; $R_1$ is methyl; and $R_2$ is t-butyl.

37. The composition of claim 28 in which R is methyl; $R_1$ is methyl; and $R_2$ is t-butyl.

38. The composition of claim 28 in which R is methyl; $R_1$ is ethyl; and $R_2$ is t-butyl.

39. The composition of claim 28 in which R is methyl; $R_1$ is n-propyl; and $R_2$ is t-butyl.

40. The composition of claim 28 in which R is ethyl; $R_1$ is n-propyl; and $R_2$ is t-butyl.

* * * * *

UNITED STATES PATENT AND TRADEMARK OFFICE
CERTIFICATE OF CORRECTION

PATENT NO. : 4,428,945
DATED : January 31, 1984
INVENTOR(S) : FAHMY, Mohamed A.

It is certified that error appears in the above-identified patent and that said Letters Patent is hereby corrected as shown below:

In the ABSTRACT, line 6, after "to", second occurrence, kindly insert --8--.

Column 2, line 66, kindly delete "formation" and insert --formulation--.

Column 4, line 22, kindly delete "0.005 ppm" and insert --0.05 ppm--.

Signed and Sealed this

Fifth Day of March 1985

[SEAL]

Attest:

DONALD J. QUIGG

Attesting Officer

Acting Commissioner of Patents and Trademarks